United States Patent [19]

Takano et al.

[11] Patent Number: 5,401,436
[45] Date of Patent: * Mar. 28, 1995

[54] OPTICALLY ACTIVE COMPOUND

[75] Inventors: Seiichi Takano, Izumi; Kunio Ogasawara, Sendai; Toshihiro Shibata, Omiya; Masaki Kimura, Tokorozawa; Norio Kurosawa, Urawa, all of Japan

[73] Assignee: Asahi Denka Kogko Kabushiki Kaisha, Tokyo, Japan

[ * ] Notice: The portion of the term of this patent subsequent to Apr. 6, 2010 has been disclaimed.

[21] Appl. No.: 989,222

[22] Filed: Dec. 11, 1992

Related U.S. Application Data

[62] Division of Ser. No. 326,540, Mar. 20, 1989, Pat. No. 5,200,111.

[30] Foreign Application Priority Data

Mar. 25, 1988 [JP] Japan .................... 62-71067

[51] Int. Cl.$^6$ ............... C09K 19/52; C09K 19/34; C07D 239/02; C07C 43/00
[52] U.S. Cl. .............. 252/299.01; 252/299.61; 252/299.64; 252/299.65; 252/299.66; 252/299.67; 544/298; 544/335; 568/585; 568/588; 568/647
[58] Field of Search ............ 252/299.01, 299.66, 252/299.61, 299.62, 299.67, 299.65, 299.64; 568/647, 585, 588; 544/298, 335

[56] References Cited

U.S. PATENT DOCUMENTS

| | | | |
|---|---|---|---|
| 4,732,699 | 3/1988 | Higuchi et al. | 252/299 |
| 4,775,223 | 10/1988 | Yoshinaga et al. | 350/333 |
| 4,786,730 | 11/1988 | Shibata et al. | 544/335 |

FOREIGN PATENT DOCUMENTS

63-307837 12/1988 Japan .
87/05018 8/1987 WIPO .

*Primary Examiner*—Shean Wu
*Attorney, Agent, or Firm*—Frishauf, Holtz, Goodman & Woodward

[57] ABSTRACT

An optically active compound of the formula (I):

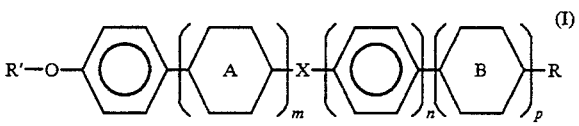

wherein

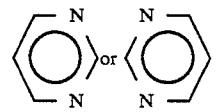

R is a halogen atom, a cyano group, an alkyl group having 1 to 18 carbon atoms, an alkoxy group having 1 to 18 carbon atoms, —R' or —O—R' group; R' is a

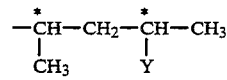

group, wherein Y is a halogen atom, a hydroxyl group, an alkoxy group having 1 to 18 carbon atoms or an acyloxy group having 1 to 18 carbon atoms; X is a direct bond or a

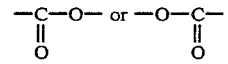

group; m, n and p each are each 0 or 1, provided that at least one of m, n and p is 1; and , represents an asymetric carbon atom. The optically active compound can impart a desired helical pitch to a liquid crystal composition

11 Claims, No Drawings

OPTICALLY ACTIVE COMPOUND

This is a division of application Ser. No. 07/326,540, filed Mar. 20, 1989, now U.S. Pat. No. 5,200,111, issued Apr. 6, 1993.

BACKGROUND OF THE INVENTION 1. (Field of the Invention)

This invention relates to a specific optically active compound. More particularly, it relates to a compound having asymmetric carbon atoms.

2. (Description of the Prior Art)

Liquid crystals are widely applied to various electrochemical devices and thus employed in practice in display devices of, for example, clocks and electric calculators. Most of liquid crystal display devices commonly used today take advantage of the dielectric alignment effects of twist-nematic or cholesteric liquid crystals. Recently, however, it has been vigorously attempted to develop liquid crystal display systems other than those mentioned above. Examples of these new systems include a STN system and a cholesteric/nematic phase transistion system.

Each liquid crystal composition to be employed in these liquid crystal display devices is adjusted in such a manner as to give the corresponding helical pitch by introducing an optically active group to nematic liquid crystals or adding an optically active substance thereto. A typical example of such a liquid crystal composition as described above is Shiff base liquid crystals prepared from a p-alkoxybenzaldehyde and (+)-p-amino-2-methylbutylbenzene. A 4-(2-methylbutyloxy)-4'-cyanobiphenyl compound is known as the optically active substance to be added to liquid crystals. However this compound is disadvantageous in that it should be added in a large amount in order to achieve the desired properties, since it has a long helical pitch of cholesteric liquid crystals.

SUMMARY OF THE INVENTION

The present inventors have conducted extensive studies in order to found an optically active compound capable of imparting the desired helical pitch to a liquid crystal mixture for a display device. As a result, they have found that a novel optically active compound represented by the following general formula (I) is highly suitable for achieving the above object.

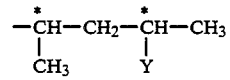  (I)

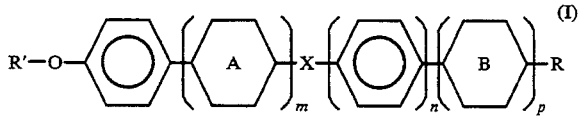

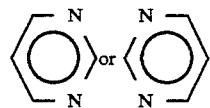

group;
R represents a halogen atom, a cyano group, an alkyl group carrying 1 to 18 carbon atoms, an alkoxy group carrying 1 to 18 carbon atoms, —R' or —O—R' group; R' represents a

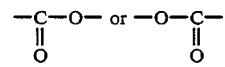

group
(wherein Y represents a halogen atom, a hydroxyl group, an alkoxy group carrying 1 to 18 carbon atoms or an acyloxy group carrying 1 to 18 carbon atoms; X represents a direct bond or a $$-\underset{\underset{O}{\|}}{C}-O-\ \text{or}\ -O-\underset{\underset{O}{\|}}{C}-$$

group;
m, n and p represent each 0 or 1, provided that at least one of m, n and p is 1; and * represents an asymmetric carbon atom.

The optically active compound of the general formula (I) of the present invention, which can impart the desired helical pitch to a liquid crystal composition and has an optically active group, is available as a component of a ferroelectric liquid crystal composition. In addition, the compound of the general formula (I) wherein R is an alkyl group carrying 6 to 18 carbon atoms is available as a ferroelectric liquid crystal per se.

DETAILED DESCRIPTION OF THE INVENTION

Examples of the halogen atom represented by R and Y in the above general formula (I) include chlorine, fluorine, bromine and iodine atoms.

Examples of the alkyl group carrying 1 to 18 carbon atoms represented by R include methyl, ethyl, propyl butyl, hexyl, octyl, dodecyl, stearyl and benzyl groups.

Examples of the alkoxy group carrying 1 to 18 carbon atoms represented by R and Y include those derived from the abovementioned alkyl groups.

Examples of the acyloxy group carrying 1 to 18 carbon atoms represented by Y include acetyloxy, propionyloxy, butyloyloxy and benzoyloxy groups.

As described above, the compound of the present invention is useful as a so-called chiral agent which imparts the desired helical pitch to a liquid crystal composition. Further it is available as a component of a ferroelectric liquid crystal composition, since it has an optically active group. Furthermore the compound of the general formula (I) wherein R is an alkyl group carrying 6 to 18 carbon atoms is available as a ferroelectric liquid crystal per se.

In addition, it is expected that the compound of the present invention has a physiological activity. Accordingly, it might be applied to, for example, drugs and agricultural chemicals.

To further illustrate the present invention, and not by way of limitation, the following Examples will be given.

Example 1

Synthesis of (R,S) 4-[4'-(3"-hydroxy-1"-methylbutoxy)phenyl]benzonitrile 0.68 g of 55% sodium hydride was mixed with 10 ml of dimethylformamide. A solution of 2.50g of 4-(4'-cyanophenyl)phenol in 5 ml of dimethylformamide was added dropwise thereto under ice-cooling. Then the obtained mixture was stirred at room temperature for one hour. A solution of 3.7 g of monotosylate of (R,R)-2,4-pentanediol in 5 ml of dimethylformamide was added dropwise thereto and the obtained mixture was stirred at 80° C. for two hours. After cooling, the reaction mixture was poured into 100 ml of ice-water and extracted with diethyl ether. After washing with water, drying and desolvating, the obtained residue was purified by silica gel column chromatography with the use of a mixture of n-hexane and ethyl acetate (3:2) as a developing solvent. Thus 1.8 g of (R,S)-4-[4'-(3''-hydroxy-1''-methylbutoxy)phenyl]benzonitrile was obtained.

The obtained product showed the following characteristic absorptions in infrared spectroscopy, which proved that it was the aimed compound.

3450 cm$^{-1}$ (m), 2970 cm$^{-1}$ (m), 2920 cm$^{-1}$ (w),
2220 cm$^{-1}$ (s), 1600 cm$^{-1}$ (vs), 1490 cm$^{-1}$ (vs),
1380 cm$^{-1}$ (w), 1300 cm$^{-1}$ (s), 1250 cm$^{-1}$ (vs),
1180 cm$^{-1}$ (s), 1120 cm$^{-1}$ (m), 1040 cm$^{-1}$ (w),
820 cm$^{-1}$ (s)

Example 2

Synthesis of (S,S)-4-[4'-(3''-chloro-1''-methylbutoxy)phenyl]benzonitrile 1.8 g of the (R,S)-4-[4'-(3''-hydroxy-1''-methylbutoxy)phenyl]benzonitrile obtained in the above Example 1 was dissolved in 36 ml of carbon tetrachloride. 3.0 g of triphenylphosphine was added thereto and the obtained mixture was stirred under reflux for five hours. After distilling off the solvent, the residue was extracted with n-hexane and desolvated. The obtained residue was purified by silica gel column chromatography with the use of a mixture of n-hexane and diethyl ether (9:1) as a developing solvent. Thus, 1.50 g of (S,S) -4-[4'-(3''-chloro-1''-methylbutoxy)phenyl]benzonitrile was obtained.

The obtained product showed the following characteristic absorptions in infrared spectroscopy, which proved that it was the aimed compound.

2970 cm$^{-1}$ (m), 2920 cm$^{-1}$ (w), 2220 cm$^{-1}$ (s),
1600 cm$^{-1}$ (vs), 1490 cm$^{-1}$ (vs), 1380 cm$^{-1}$ (m),
1300 cm$^{-1}$ (s), 1250 cm$^{-1}$ (vs), 1180 cm$^{-1}$ (s),
1140 cm$^{-1}$ (m), 1040 cm$^{-1}$ (m), 820 cm$^{-1}$ (s),
610 cm$^{-1}$ (w)

Example 3

Synthesis of (R,S)-4-[4'-(3''-methoxy-1''-methylbutoxy)phenyl]benzonitrile 0.13 g of 55% sodium hydride was mixed with 1 ml of dimethylformamide. A solution of 0.56 g of the (R,S)-4-[4'-( 3''-hydroxy-1''-methylbutoxy)phenyl]benzonitrile prepared in the above Example 1 in 2 ml of dimethylformamide was added dropwise thereto under ice-cooling. The obtained mixture was then stirred at room temperature for one hour. Subsequently a solution of 0.36 g of methyl iodide in 2 ml of dimethylformamide was added thereto and the obtained mixture was stirred at room temperature for two hours. 10 ml of water was carefully added to the reaction mixture and the obtained mixture was extracted with diethyl ether. After thoroughly washing with water, drying and desolvating, the obtained residue was purified by silica gel column chromatography, similar to the case of Example 1, with the use of a mixture of n-hexane and ethyl acetate (4:1) as a developing solvent. Thus 0.36 g of the title compound, namely, (R,S)-4-[4'-(3''-methoxy-1''-methylbutoxy)phenyl]benzonitrile was obtained.

The obtained product showed the following characteristic absorptions in infrared spectroscopy, which proved that it was the aimed compound.

2970 cm$^{-1}$ (m), 2920 cm$^{-1}$ (m), 2210 cm$^{-1}$ (s),
1600 cm$^{-1}$ (vs), 1490 cm$^{-1}$ (vs), 1375 cm$^{-1}$ (m),
1280 cm$^{-1}$ (m), 1240 cm$^{-1}$ (vs), 1180 cm$^{-1}$ (s),
1100 cm$^{-1}$ (m), 1030 cm$^{-1}$ (m), 820 cm$^{-1}$ (s)

Example 4

Synthesis of (R,S)-4-[4'-(3''-acetoxy-1''-methylbutoxy)phenyl]benzonitrile 2.81 g of the (R,S)-4-[4'-(3''-hydroxy-1''-methylbutoxy)phenyl]benzonitrile prepared in the above Example 1 was mixed with 5.10 g of acetic anhydride and 0.3 g of pyridine. The mixture was stirred at 100° C. for one hour. After cooling, the reaction mixture was carefully poured into 50 ml of 2N hydrochloric acid and extracted with diethyl ether. After washing with water, drying and desolvating, the obtained residue was purified by silica gel column chromatography with the use of a mixture of n-hexane and ethyl acetate (3:1) as a developing solvent. Thus 2.65 g of (R,S)-4-[4'-(3''-acetoxy-1''methylbutoxy)phenyl]benzonitrile was obtained.

The obtained product showed the following characteristic absorptions in infrared spectroscopy, which proved that it was the aimed compound.

2970 cm$^{-1}$ (m), 2920 cm$^{-1}$ (w), 2210 cm$^{-1}$ (s),
1730 cm$^{-1}$ (vs), 1600 cm$^{-1}$ (vs), 1490 cm$^{-1}$ (vs),
1370 cm$^{-1}$ (m), 1280 cm$^{-1}$ (s), 1240 cm$^{-1}$ (vs),
1180 cm$^{-1}$ (m), 1100 cm$^{-1}$ (m), 1030 cm$^{-1}$ (m),
820 cm$^{-1}$ (s)

Example 5

Synthesis of (S,S)-4-[4'-(3''-acetoxy-1''-methylbutoxy)phenyl]benzonitrile 0.50 g of the (R,S) -4-[4'-(3''-hydroxy-1''-methylbutoxy)phenyl]benzonitrile obtained in the above Example 1 was mixed with 0.12 g of acetic anhydride, 0.51 g of triphenylphosphine and 5 ml of ethyl ether. To the obtained mixture, was added dropwise 0.34 g of diethyl azodicarboxylate under stirring. The obtained mixture was stirred at room temperature for three hours. The triphenylphosphine oxide thus precipitated was filtered and desolvated to thereby give a crude product which was purified by silica gel column chromatography with the use of a mixture of ethyl acetate and n-hexane (1:3) as a developing solvent. Thus 0.18 g of the title compound as obtained. The obtained product showed the following characteristic absorptions in infrared spectroscopy, which proved that it was the aimed compound.

2970 cm$^{-1}$ (m), 2920 cm$^{-1}$ (m), 2210 cm$^{-1}$ (s),
1725 cm$^{-1}$ (vs), 1600 cm$^{-1}$ (vs), 1485 cm$^{-1}$ (vs),
1365 cm$^{-1}$ (s), 1280 cm$^{-1}$ (s), 1240 cm$^{-1}$ (vs),
1180 cm$^{-1}$ (s), 1100 cm$^{-1}$ (s), 1040 cm$^{-1}$ (m),
820 cm$^{-1}$ (s)

Example 6

Synthesis of
(S,S)-4-(3'-chloro-1'-methylbutoxy)benzoic
acid-4-cyanophenyl ester 1.00 g of 4-(3'-chloro-1'-methylbutoxy)benzoic acid, 0.50 g of 4-cyanophenol, 0.93 g of dicyclohexylcarbodiimide, 0.10 g of 4-pyrrolydinopyridine and 10 ml of methylene chloride were stirred together at room temperature for five hours. The dicyclohexyl urea thus precipitated was filtered and the filtrate was desolvated. The crude product thus obtained was purified by silica gel column chromatography with the use of a mixture of ethyl acetate and n-hexane (1:4) as a developing solvent to thereby give the title compound.

The obtained product showed the following characteristic absorptions in infrared spectroscopy, which proved that it was the aimed compound.

2980 cm$^{-1}$ (m), 2220 cm$^{-1}$ (m), 1730 cm$^{-1}$ (vs), 1600 cm$^{-1}$ (vs), 1505 cm$^{-1}$ (s), 1250 cm$^{-1}$ (vs), 1205 cm$^{-1}$ (vs), 1180 cm$^{-1}$ (s), 1075 cm$^{-1}$ (s),

Example 7

Synthesis of
(S,S)-4-[4'-(3''-chloro-1''-methylbutoxy)phenyl]benzoic
acid-4-cyanophenyl ester Methyl (R, S) -4-[4'-( 3''-hydroxy-1''-methylbutoxy)-phenyl]benzoate, which had been obtained from methyl 4(4'-Hydroxyphenyl)benzoate and monotosylate of (R,R)-2,4-pentadiol, was chlorinated and hydrolyzed. 0.5 g of the (S,S)-4-[4'-(3''-chloro-1''-methylbutoxy)-phenyl]benzoic acid thus obtained, 0.199 of 4-cyanophenol, 0.04 g of 4-pyrrolidinopyridine, 0.34 g of dicycylohexylcarbodiimide and 6 ml of methylene chloride were stirred at room temperature for five hours. The dicyclohexyl urea thus precipitated was filtered and the filtrate was desolvated. The obtained crude product was recrystallized from ethyl alcohol to thereby give 0.4 g of the title compound (m.p. :103.8° C.).

The obtained product showed the following characteristic absorptions in infrared spectroscopy, which proved that it was the aimed compound.

3000 cm$^{-1}$ (m), 2930 cm$^{-1}$ (m), 2210 cm$^{-1}$ (m), 1740 cm$^{-1}$ (s), 1600 cm$^{-1}$ (s), 1500 cm$^{-1}$ (s), 1400 cm$^{-1}$ (w), 1270 cm$^{-1}$ (s), 1200 cm$^{-1}$ (s), 1070 cm$^{-1}$ (s), 1020 cm$^{-1}$ (m), 950 cm$^{-1}$ (w), 880 cm$^{-1}$ (m), 820 cm$^{-1}$ (m), 760 cm$^{-1}$ (m)

Example 8

Synthesis of
(S,S)-4-(3'-chloro-1'-methylbutoxy)benzoic
acid-4-cyanobiphenyl ester Methyl (R,S)-4-(3'-hydroxy-1'-methylbutoxy)benzoic acid, which had been obtained from methyl 4-hydroxybenzoate and monotosylate of (R,R)-2,4-pentanediol, was chlorinated and hydrolyzed. 1.00 g of the (S,S)-4-(3'-chloro-1'-methylbutoxy)benzoic acid thus obtained, 0.80 g of 4-(4'-cyanophenyl)phenol, 0.10 g of 4-pyrrolidinopyridine, 0.9 g of dicyclohexylcarbodiimide and 10 ml of methylene chloride were stirred together at room temperature for five hours. The dicyclohexyl urea thus precipitated was filtered and the filtrate was desolvated. The crude product thus obtained was recrystallized from ethyl alcohol to thereby give 1.01 g of (S,S)-4-(3''-chloro-1'-methylbutoxy)benzoic acid-4-cyanobiphenyl ester (m.p.: 125° C.) .

The obtained product showed the following characteristic absorptions in infrared spectroscopy, which proved that it was the aimed compound.

2970 cm$^{-1}$ (m), 2920 cm$^{-1}$ (w), 2210 cm$^{-1}$ (m), 1720 cm$^{-1}$ (s), 1600 cm$^{-1}$ (s), 1500 cm$^{-1}$ (m), 1490 cm$^{-1}$ (m), 1375 cm$^{-1}$ (w), 1260 cm$^{-1}$ (s), 1210 cm$^{-1}$ (s), 1165 cm$^{-1}$ (s), 1090 cm$^{-1}$ (m), 820 cm$^{-1}$ (m), 760 cm$^{-1}$ (m)

Example 9

Synthesis of
(S,S)-4-(3'-chloro-1'-methylbutoxy)benzoic
acid-4-n-propylphenyl ester The procedure of Example 6 was repeated except that the 4-(4'-cyanophenyl)phenol was substituted with 4-n-propylphenol. The residue was purified by silica gel column chromatography with the use of a mixture of ethyl acetate and n-hexane (3:7) as a developing solvent to thereby give the title compound.

The obtained product showed the following characteristic absorptions in infrared spectroscopy, which proved that it was the aimed compound.

2960 cm$^{-1}$ (m), 2930 cm$^{-1}$ (m), 2860 cm$^{-1}$ (w), 1730 cm$^{-1}$ (s), 1600 cm$^{-1}$ (s), 1510 cm$^{-1}$ (s), 1380 cm$^{-1}$ (m), 1250 cm$^{-1}$ (vs), 1200 cm$^{-1}$ (vs), 1170 cm$^{-1}$ (vs), 1070 cm$^{-1}$ (s), 1030 cm$^{-1}$ (m), 760 cm$^{-1}$ (m)

Example 10

Synthesis of
(S,S)-4-[4'-(3''-chloro-1''-methylbutoxy)phenyl]benzoic
acid-4-n propylphenyl ester 0.47 g of (S,S)-4-[4'-(3''-chloro-1''-methylbutoxy)-phenyl]benzoic acid, 0.20 g of 4-n-propylphenol, 0.32 g of dicyclohexylcarbodiimide, 0.04 g of 4-pyrrolidinopyridine and 6 ml of methylene chloride were stirred together at room temperature for five hours. The dicyclohexyl urea thus precipitated was filtered and the filtrate was desolvated. The crude product thus obtained was purified by silica gel column chromatography with the use of a mixture of n-hexane and ethyl acetate (17:3) as a developing solvent. Thus 0.4 g of the title compound was obtained.

The obtained product showed the following characteristic absorptions in infrared spectroscopy which proved that it was the aimed compound.

2970 cm$^{-1}$ (s), 2950 cm$^{-1}$ (s), 2880 cm$^{-1}$ (m), 1740 cm$^{-1}$ (s), 1600 cm$^{-1}$ (s), 1510 cm$^{-1}$ (s), 1500 cm$^{-1}$ (s), 1450 cm$^{-1}$ (m), 1400 cm$^{-1}$ (m), 1380 cm$^{-1}$ (m), 1280 cm$^{-1}$ (s), 1190 cm$^{-1}$ (s), 1080 cm$^{-1}$ (s), 1040 cm$^{-1}$ (s), 960 cm$^{-1}$ (m), 830 cm$^{-1}$ (s), 770 cm$^{-1}$ (s)

Example 11

Synthesis of
(S,S)-4-[4'-(3''-chloro-1''-methylbutoxy)phenyl]benzoic
acid-4-ethoxyphenyl ester 0.72 g of (S,S)-4-[3'-chloro-1'-methylbotoxy)phenyl]-benzoic acid, 0.28 g of 4-ethoxyphenol, 0.45 g of dicyclohexylcarbodiimide, 0.05 g of 4-pyrrolidinopyridine and 20 ml of methylene chloride were stirred together at room temperature for four hours. The dicyclohexyl urea thus precipitated was filtered and the filtrate was desolvated. The crude product thus obtained was purified by silica gel column chromatography with the use of a mixture of n-hexane and ethyl acetate (9:1) as a developing solvent to thereby give the title compound.

The obtained product showed the following characteristic absorptions in infrared spectroscopy, which proved that it was the aimed compound.

2980 cm$^{-1}$ (w), 1730 cm$^{-1}$ (s), 1605 cm$^{-1}$ (s),
1505 cm$^{-1}$ (s), 1395 cm$^{-1}$ (w), 1295 cm$^{-1}$ (s),
1275 cm$^{-1}$ (s), 1245 cm$^{-1}$ (s), 1200 cm$^{-1}$ (s),
1120 cm$^{-1}$ (w), 1085 cm$^{-1}$ (m), 1050 cm$^{-1}$ (w),
875 cm$^{-1}$ (w), 835 cm$^{-1}$ (w), 815 cm$^{-1}$ (w),
770 cm$^{-1}$ (m), 525 cm$^{-1}$ (w)

Example 12

Synthesis of (S,S)-4-(3'-chloro-1'-methylbutoxy)benzoic acid-4-(4'-n-butoxyphenyl)phenyl ester 0.21 g of (S, S)-4-(3'-chloro-1'-methylbutoxy)benzoic acid, 0.21 g of 4-n-butoxyphenyl phenol, 0.19 g of dicyclohexylcarbodiimide, 0.03 g of 4-pyrrolidinopyridene and 6 ml of methylene chloride were stirred together at room temperature for five hours. The dicyclohexyl urea thus precipitated was filtered and the filtrate was desolvated. The crude product thus obtained was purified by silica gel column chromatography with the use of a mixture of n-hexane and ethyl acetate (9:1) as a developing solvent to thereby give 0.2 g of the title compound.

The obtained product showed the following characteristic absorptions in infrared spectroscopy, which proved that it was the aimed compound.

3000 cm$^{-1}$ (s), 2950 cm$^{-1}$ (s), 2850 cm$^{-1}$ (m),
1740 cm$^{-1}$ (s), 1600 cm$^{-1}$ (s), 1500 cm$^{-1}$ (s),
1370 cm$^{-1}$ (m), 1305 cm$^{-1}$ (m), 1250 cm$^{-1}$ (s),
1200 cm$^{-1}$ (s), 1150 cm$^{-1}$ (s), 1060 cm$^{-1}$ (s),
1020 cm$^{-1}$ (m), 860 cm$^{-1}$ (m), 800 cm$^{-1}$ (m),
760 cm$^{-1}$ (s)

Example 13

Synthesis of (S,S)-4-cyanobenzoic acid4-[4'-(3''-chloro-1''-methylbutoxy)phenyl]phenyl ester 0.30 g of (S,S)-4-[4-(3''-chloro-1''-methylbutoxy)-phenyl]phenol, 0.16 g of 4-cyanobenzoic acid, 0.22 g of dicyclohexylcarbodiimide, 0.04 g of 4-pyrrolidinopyridine and 6 ml of methylene chloride were stirred together at room temperature for five hours. The dicyclohexyl urea thus precipitated was filtered and the filtrate was desolvated. The crude product thus obtained was purified by silica gel column chromatography with the use of a mixture of n-hexane and ethyl acetate (7:3) as a developing solvent to thereby give 0.2 g of the title compound.

The obtained product showed the following characteristic absorptions in infrared spectroscopy, which proved that it was the aimed compound.

2980 cm$^{-1}$ (s), 2940 cm$^{-1}$ (m), 2250 cm$^{-1}$ (s),
1740 cm$^{-1}$ (s), 1600 cm$^{-1}$ (s), 1500 cm$^{-1}$ (s),
1380 cm$^{-1}$ (m), 1250 cm$^{-1}$ (s), 1200 cm$^{-1}$ (s),
1170 cm$^{-1}$ (s), 1080 cm$^{-1}$ (s), 950 cm$^{-1}$ (m),
830 cm$^{-1}$ (s), 760 cm$^{-1}$ (s)

Example 14

Synthesis of (S, S)-4-n-propylbenzoic acid-4[4'-(3''-chloro-1''-methylbutoxy)phenyl]phenyl ester The procedure of Example 13 was repeated except that the 4-cyanobenzoic acid was substituted with 0.17 g of 4-n-propylbenzoic acid. The crude product thus obtained was purified by silica gel column chromatography with the use of a mixture of n-hexane and ethyl acetate (9:1) as a developing solvent to thereby give the title compound.

The obtained product showed the following characteristic absorptions in infrared spectroscopy, which proved that it was the aimed compound.

3050 cm$^{-1}$ (m), 2980 cm$^{-1}$ (s), 2950 cm$^{-1}$ (s),
1740 cm$^{-1}$ (s), 1605 cm$^{-1}$ (s), 1495 cm$^{-1}$ (s),
1380 cm$^{-1}$ (m), 1260 cm$^{-1}$ (m), 1250 cm$^{-1}$ (m),
1200 cm$^{-1}$ (s), 1080 cm$^{-1}$ (s), 1020 cm$^{-1}$ (m),
820 cm$^{-1}$ (s), 760 cm$^{-1}$ (s)

Example 15

Synthesis of (S,S)-4-methoxybenzoic acid 4[4'-(3''-chloro-1''-methylbutoxy)phenyl]phenyl ester The procedure of Example 13 was repeated except that the 4-cyanobenzoic acid was substituted with 0.17 g of 4-methoxybenzoic acid. The crude product thus obtained was purified by silica gel column chromatography with the use of a mixture of n-hexane and ethyl acetate (9:1) as a developing solvent and then recrystallized from ethyl alcohol. Thus the title compound was obtained (m.p.:82° C.).

The obtained product showed the following characteristic absorptions in infrared spectroscopy, which proved that it was the aimed compound.

3000 cm$^{-1}$ (s), 2950 cm$^{-1}$ (s), 1740 cm$^{-1}$ (s),
1600 cm$^{-1}$ (s), 1500 cm$^{-1}$ (s), 1380 cm$^{-1}$ (m),
1260 cm$^{-1}$ (s), 1205 cm$^{-1}$ (s), 1180 cm$^{-1}$ (s),
1080 cm$^{-1}$ (s), 1040 cm$^{-1}$ (s), 960 cm$^{-1}$ (m),
850 cm$^{-1}$ (s), 820 cm$^{-1}$ (s), 760 cm$^{-1}$ (s),

Example 16

Synthesis of (S,S)-4-(4'-methoxyphenyl)benzoic acid-4-(3'-chloro-1'-methylbutoxy)phenyl ester 0.50 g of 4-(4'-methoxyphenyl)benzoic acid, 0.44 g of (S,S)-4-(3'-chloro-1'-methylbutoxy)phenol, 0.45 g of dicyclohexylcarbodiimide, 0.05 g of 4-pyrrolidinopyridine and 20 ml of methylene chloride were stirred together at room temperature for five hours. The crude product obtained in the same manner as the one described in Example 8 was purified by silica gel column chromatography with the use of a mixture of n-hexane and ethyl acetate (85:15) as a developing solvent and recrystallized from ethyl alcohol to thereby give the title compound.

The obtained product showed the following characteristic absorptions in infrared spectroscopy, which proved that it was the aimed compound.

3000 cm$^{-1}$ (w), 2950 cm$^{-1}$ (w), 1730 cm$^{-1}$ (s),
1605 cm$^{-1}$ (s), 1505 cm$^{-1}$ (s), 1440 cm$^{-1}$ (w),
1380 cm$^{-1}$ (w), 1275 cm$^{-1}$ (s), 1255 cm$^{-1}$ (s),
1190 cm$^{-1}$ (s), 1140 cm$^{-1}$ (w), 1080 cm$^{-1}$ (s),
1040 cm$^{-1}$ (w), 1020 cm$^{-1}$ (w), 875 cm$^{-1}$ (w),
835 cm$^{-1}$ (w), 775 cm$^{-1}$ (m), 705 cm$^{-1}$ (w),
610 cm$^{-1}$ (w), 535 cm$^{-1}$ (w)

Example 17

Synthesis of (S,S)-4-(4'-n-octyloxyphenyl)benzoic acid-4-(3'-chloro-1'-methylbutoxy)phenyl ester 0.36 g of 4-(4'-n-octyloxyphenyl)benzoic acid, 0.21 g of (S,S)-4-(3'-chloro-1'-methylbutoxy)phenol, 0.02 g of 4-pyrrolidinopyridine, 0.21 g of dicyclohexylcarbodiimide and 10 ml of methylene chloride were stirred together at room temperature for four hours. The dicyclohexyl urea thus precipitated was filtered and the filtrate was desolvated. The obtained residue was purified by silica gel column chromatography with the use of a mixture of n-hexane and ethyl acetate (9:1) as a developing solvent to thereby give the title compound.

The obtained product showed the following characteristic absorptions in infrared spectroscopy, which proved that it was the aimed compound.

2950 cm$^{-1}$ (s), 2870 cm$^{-1}$ (m), 1730 cm$^{-1}$ (s),
1605 cm$^{-1}$ (s), 1505 cm$^{-1}$ (s), 1470 cm$^{-1}$ (w),
1300 cm$^{-1}$ (s), 1270 cm$^{-1}$ (s), 1245 cm$^{-1}$ (w),
1200 cm$^{-1}$ (s), 1145 cm$^{-1}$ (w), 1080 cm$^{-1}$ (s),
1040 cm$^{-1}$ (m), 1015 cm$^{-1}$ (w), 870 cm$^{-1}$ (w),
835 cm$^{-1}$ (m), 770 cm$^{-1}$ (m), 615 cm$^{-1}$ (w),
525 cm$^{-1}$ (w)

This compound was put between two glass plates and observed under a polarization microscope. As a result, the following phase transition was confirmed.

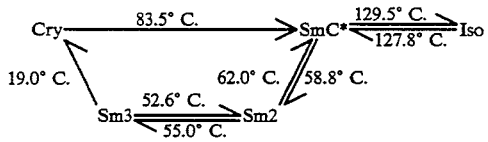

Separately, this compound was poured into a transparent glass electrode cell of 2 μm in thickness, which had been aligned by rubbing, at 150° C. and then heated to thereby give an isotropic liquid. The liquid crystal cell thus obtained was slowly cooled to 65° C. and a rectangular wave (±30 V, 1 Hz) was applied thereto under crossed Nicol's prisms. Thus an obvious switching was observed at a response rate of 220 usec.

Example 18

Synthesis of (S,S)-4-(3'-chloro-1'-methylbutoxy) benzoic acid-4-(5'-n-hexyl-2'-pyrimidyl)phenyl ester The procedure of Example 6 was repeated except that the 4-(4'-cyanophenyl)phenol was substituted with 5-n-hexyl-2-pyrimidylphenol to thereby give the title compound.

The obtained product showed the following characteristic absorptions in infrared spectroscopy, which proved that it was the aimed compound.

2920 cm$^{-1}$ (s), 2850 cm$^{-1}$ (m), 1730 cm$^{-1}$ (s),
1600 cm$^{-1}$ (s), 1580 cm$^{-1}$ (m), 1540 cm$^{-1}$ (m),
1500 cm$^{-1}$ (s), 1420 cm$^{-1}$ (vs), 1250 cm$^{-1}$ (vs),
1200 cm$^{-1}$ (vs), 1160 cm$^{-1}$ (vs) 1070 cm$^{-1}$ (s),
1055 cm$^{-1}$ (s), 760 cm$^{-1}$ (w)

Example 19

Synthesis of (R,S)-2-(4'-n-octylphenyl)-5-[4'-(3"-hydroxy-1"-methylbutoxy)phenyl]pyrimidine 0.15 g of 55% sodium hydride was mixed with 3 ml of dimethylformamide. A solution of 1.00 g of 4-[2'-(4"-n-octylphenyl)-5-pyrimidinyl]phenol in 2 ml of dimethylformamide was added dropwise thereto under ice-cooling. After the completion of the addition, the obtained mixture was stirred at room temperature for one hour. Then, a solution of 0.79 g of monotosylate of (R,R)-2,4-pentadediol in 2 ml of dimethylformamide was added dropwise thereto and the mixture was stirred at 80° C. for 1.5 hour. After cooling, the reaction mixture was poured into 100 ml of ice-water and extracted with diethyl ether. After washing with water and desolvating, the residue was purified by silica gel column chromatography with the use of a mixture of ethyl acetate and n-hexane (3:7) as a developing solvent to thereby give 0.76 g of the title compound. The obtained product showed the following characteristic absorptions in infrared spectroscopy, which proved that it was the aimed compound.

3400 cm$^{-1}$ (m), 2910 cm$^{-1}$ (s), 2840 cm$^{-1}$ (m),
1605 cm$^{-1}$ (m), 1580 cm$^{-1}$ (m), 1520 cm$^{-1}$ (w),
1510 cm$^{-1}$ (m), 1430 cm$^{-1}$ (vs), 1240 cm$^{-1}$ (s),
835 cm$^{-1}$ (m), 790 cm$^{-1}$ (w)

Example 20

Synthesis of (S,S)-2-(4'-n-octylphenyl)-5-[4'-(3"-chloro-1"-methylbutoxy)phenyl]pyrimidine 0.50 g of the compound obtained in the above Example 19 was dissolved in 10 ml of carbon tetrachloride and 0.53 g of triphenylphosphine was added thereto. The obtained mixture was stirred under reflux for five hours.

After distilling off the solvent, the residue was extracted with hexane and desolvated. The obtained residue was purified by silica gel column chromatography with the use of a mixture of diethyl ether and n-hexane (1:4) as a developing solvent to thereby give 0.38 g of the title compound.

The obtained product showed the following characteristic absorptions in infrared spectroscopy, which proved that it was the aimed compound.

2930 cm$^{-1}$ (s), 2850 cm$^{-1}$ (m), 1605 cm$^{-1}$ (m),
1580 cm$^{-1}$ (w), 1525 cm$^{-1}$ (w), 1510 cm$^{-1}$ (m),
1430 cm$^{-1}$ (vs), 1240 cm$^{-1}$ (s), 840 cm$^{-1}$ (m),
790 cm$^{-1}$ (w)

Example 21

Synthesis of (S,S,S,S)-4-[4'-(3"-chloro-1"-methylbutoxy)phenyl]-benzoic acid-3-chloro-1-methylbutyl ester 1.93 g of (R,S,R,S)-4-[4'-(3"-hydroxy-1"-methylbutoxy)phenyl]benzoic acid-3-hydroxyl-1-methylbutyl ester, which had been obtained by etherifying and esterifying 4-(4'-hydroxyphenyl) benzoic acid and (R,R)-2,4-pentanediol, and 4.7 g of triphenylphosphine were dissolved in carbon tetrachloride and stirred under reflux for five hours. After distilling off the solvent, 50 ml of n-hexane was added thereto. The triphenylphosphine oxide thus precipitated was filtered and the filtrate was desolvated and purified by silica gel column chromatography with the use of a mixture of n-hexane and ethyl acetate (8:2) as a developing solvent to thereby give the title compound.

The obtained product showed the following characteristic absorptions in infrared spectroscopy, which proved that it was the aimed compound.

2980 cm$^{-1}$ (s), 2930 cm$^{-1}$ (m), 1710 cm$^{-1}$ (s),
1605 cm$^{-1}$ (s), 1580 cm$^{-1}$ (w), 1490 cm$^{-1}$ (s),
1260 cm$^{-1}$ (s), 1185 cm$^{-1}$ (s), 1105 cm$^{-1}$ (s),
1030 cm$^{-1}$ (m)

Example 22

Synthesis of (S,S,S,S)-4-[4'-(3"-chloro-1"-methylbutoxy)phenyl]-benzoic acid-4-(3'-chloro-1'-methylbutoxy)phenyl ester 0.44 g of (S,S)-4-(3'-chloro-1'-methylbutoxy) phenol, 0.72 g of (S,S)-4-[4'-(3"chloro-1"-methylbutoxy)benzoic acid, 0.45 g of N,N'-dicyclohexylcarbodimide, 0.05 g of 4-pyrrolidinopyridine and 20 ml of methylene chloride were stirred together at room temperature for four hours. The dicyclohexyl urea thus precipitated was filtered and the filtrate was desolvated. The crude product thus obtained was purified by silica gel column chromatography with the use of a mixture of n-hexane and ethyl acetate (9:1) as a developing solvent and recrystallized from ethyl alcohol to thereby give the title compound.

The obtained product showed the following characteristic absorptions in infrared spectroscopy, which proved that it was the aimed compound.

2980 cm$^{-1}$ (w), 2940 cm$^{-1}$ (w), 1730 cm$^{-1}$ (s),
1605 cm$^{-1}$ (s), 1505 cm$^{-1}$ (s), 1445 cm$^{-1}$ (w),
1380 cm$^{-1}$ (w), 1275 cm$^{-1}$ (s), 1245 cm$^{-1}$ (s),
1190 cm$^{-1}$ (s), 1140 cm$^{-1}$ (w), 1080 cm$^{-1}$ (s),
1040 cm$^{-1}$ (w), 830 cm$^{-1}$ (w), 815 cm$^{-1}$ (w),
770 cm$^{01}$ (m), 605 cm$^{-1}$ (w)

Example 23

Synthesis of (S,S,S,S)-4-(3'-chloro-1'-methylbutoxy) benzoic acid-4-[4'-(3''-chloro-1''-methylbutoxy)phenyl]phenyl ester 0.30 g of (S,S)-4-[4'-(3''-chloro-1''-methylbutoxy)phenyl]phenol, 0.24q of (S,S)-4-(3'-chloro-1'-methylbutoxy)benzoic acid, 0.22 g of dicyclocarbodiimide, 0.04 g of 4-pyrrolidinopyridine and 6 ml of methylene chloride were stirred together at room temperature for five hours. The dicyclohexyl urea thus precipitated was filtered and the filtrate was desolvated. The crude product thus obtained was purified by silica gel column chromatography with the use of a mixture of n-hexane and ethyl acetate (4:1) as a developing solvent to thereby give 0.2 g of the title compound.

The obtained product showed the following characteristic absorptions in infrared spectroscopy, which proved that it was the aimed compound.

2950 cm$^{-1}$ (s), 2900 cm$^{-1}$ (s), 1740 cm$^{-1}$ (s),
1600 cm$^{-1}$ (s), 1500 cm$^{-1}$ (s), 1360 cm$^{-1}$ (s),
1200 cm$^{-1}$ (s), 1060 cm$^{-1}$ (s), 950 cm$^{-1}$ (m),
900 cm$^{-1}$ (m), 880 cm$^{-1}$ (m), 810 cm$^{-1}$ (m),
760 cm$^{-1}$ (m)

Referential Example

1% by weight of each compound obtained in the above Examples was added to ZLI-1565, which is a typical nematic liquid crystal compound mfd. by Merck Co., Inc. The pitch of the obtained mixture was measured in a Kano wedge cell at 30° C. and 60° C. The following table shows the results

| Test compound | Pitch (μm) 30° C. | 60° C. |
|---|---|---|
| none | — | — |
| Ex. 1 | 17.4 | 19.4 |
| Ex. 2 | 7.4 | 7.4 |
| Ex. 3 | 26.0 | 23.4 |
| Ex. 4 | 36.4 | 35.8 |
| Ex. 5 | 30.2 | 22.6 |
| Ex. 6 | 16.0 | 16.0 |
| Ex. 7 | 8.2 | 7.8 |
| Ex. 8 | 7.8 | 7.4 |
| Ex. 9 | 9.6 | 9.8 |
| Ex. 10 | 7.6 | 7.2 |
| Ex. 11 | 12.0 | 11.0 |
| Ex. 16 | 11.0 | 10.6 |
| Ex. 17 | 10.6 | 9.8 |
| Ex. 18 | 8.8 | 8.6 |
| Ex. 19 | 50.0 | 70.0 |
| Ex. 20 | 9.8 | 9.2 |
| Ex. 21 | 10.4 | 11.0 |
| Ex. 22 | 5.8 | 5.2 |

The above table obviously indicates that the compound of the present invention is highly useful as a chiral compound capable of imparting the desired pitch to a liquid crystal composition.

What is claimed is:

1. An optically active compound represented by the following formula (I):

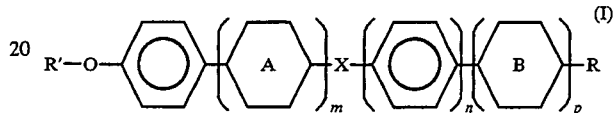

wherein 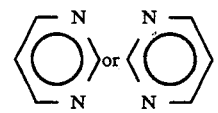 and B are each a 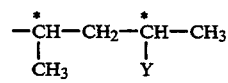,

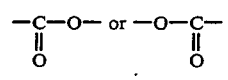

group;
R represents a halogen atom, a cyano group, an alkyl group carrying 1 to 18 carbon atoms, an alkoxy group carrying 1 to 18 carbon atoms, —R' or —O—R' group; R' represents a $$-\overset{*}{C}H-CH_2-\overset{*}{C}H-CH_3$$
$$\phantom{-}\underset{CH_3}{|}\phantom{-CH_2-}\underset{Y}{|}$$

group,
wherein Y represents a chlorine atom or an alkanoyloxy group having 1 to 18 carbon atoms; X represents a direct bond or a $$-\underset{\underset{O}{||}}{C}-O- \text{ or } -O-\underset{\underset{O}{||}}{C}-$$

group;
m, n and p each represent 0 to 1, provided that at least one of m, n and p is 1; and * represents an asymmetric carbon atom.

2. An optically active compound as set forth in claim 1, wherein R is a cyano group.

3. An optically active compound as set forth in claim 1, wherein R is a n-alkyl group carrying 1 to 18 carbon atoms.

4. An optically active compound as set forth in claim 1, wherein R is a n-alkoxy group carrying 1 to 18 carbon atoms.

5. An optically active compound as set forth in claim 1, wherein X is a direct bond.

6. An optically active compound as set forth in claim 1, wherein X is a

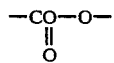

group.

7. An optically active compound as set forth in claim 1, wherein m+n+p is 1.

8. An optically active compound as set forth in claim 1, wherein m+n+p is 2.

9. A nematic liquid crystal composition comprising an optically active compound as set forth in claim 1 and a nematic liquid crystal compound.

10. An optically active compound as set forth in claim 1, wherein R is selected from the group consisting of chlorine, bromine, iodine, methyl, ethyl, propyl, butyl, hexyl, octyl and dodecyl.

11. An optically active compound as set forth in claim 10, wherein Y is selected from the group consisting of chlorine, acetyloxy, propionyloxy, butyloyloxy.

* * * * *